United States Patent [19]

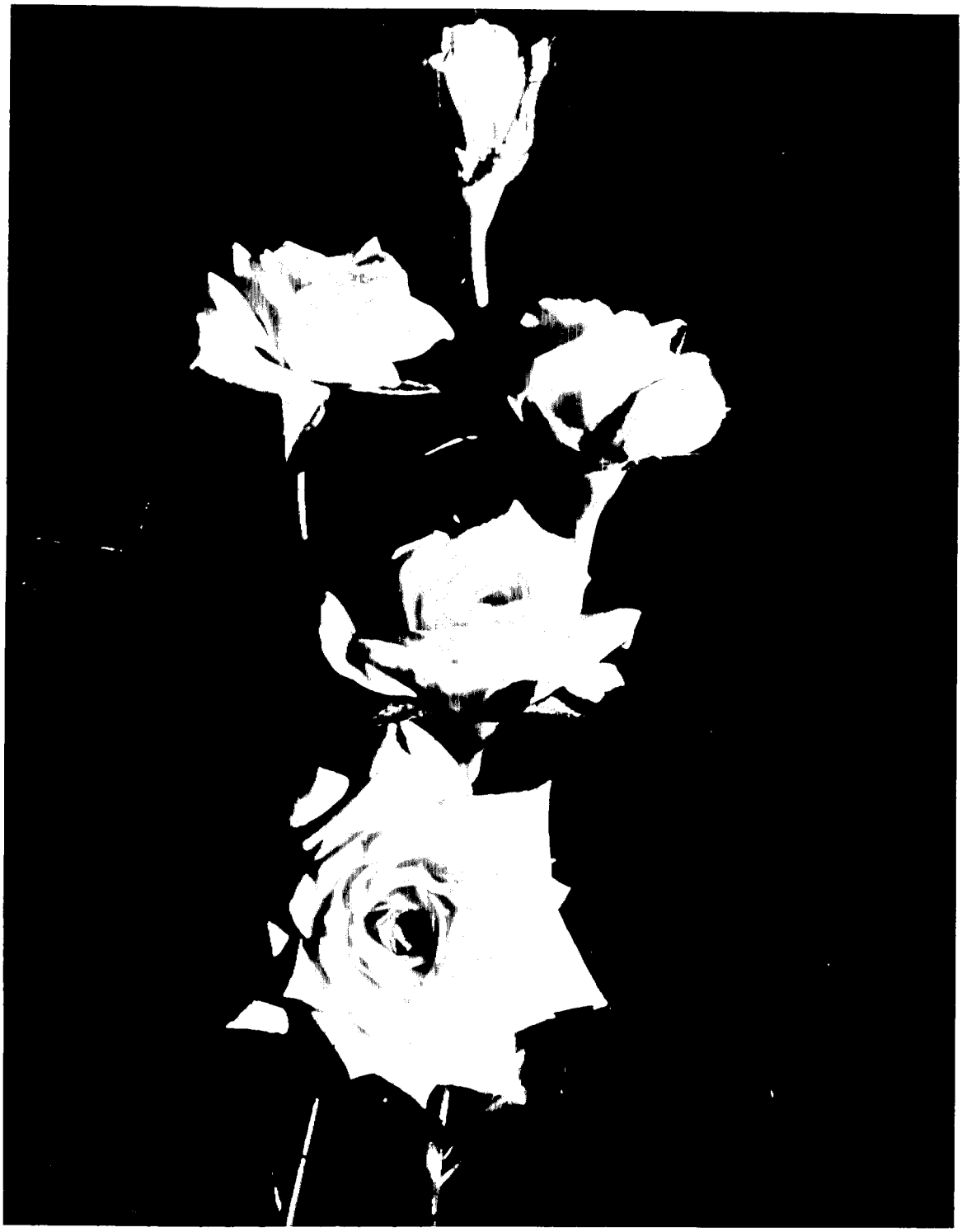

Williams

[11] Patent Number: Plant 5,631

[45] Date of Patent: Jan. 14, 1986

[54] MINIATURE ROSE VARIETY 'MINOCO'

[75] Inventor: Ernest D. Williams, Dallas, Tex.

[73] Assignee: Mary Kay Cosmetics, Inc., Dallas, Tex.

[21] Appl. No.: 605,579

[22] Filed: Apr. 30, 1984

[51] Int. Cl.[4] ..... A01H 5/00

[52] U.S. Cl. ..... Plt./9

[58] Field of Search ..... Plt./9

*Primary Examiner*—James R. Feyrer

*Attorney, Agent, or Firm*—Vincent G. Gioia

[57] ABSTRACT

A new miniature rose variety of azalea pink flower coloring.

1 Drawing Figure

1

The present invention relates to a new and distinct variety of rose plant of the miniature rose class, which was originated by my crossing as seed parent the rose known as "Tom Brown" and the rose known as "Over the Rainbow" (U.S. Plant Pat. No. 3,472) as pollen parent. The denomination of the new rose is "Minoco".

Among the novel characteristics possessed by this new variety which distinguish it from its parent and all other varieties of which I am aware are its attractive flowers of good form and azalea pink coloring and unusual combination of inner petals rolling downward and outer petals reflexing to points. The flower coloring is constant and substantially unfading. Asexual reproduction by budding of the new variety as performed in Dallas County, Tex., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "13B" is plate 13B of The Royal Horticultural Society Colour Chart.

Parentage: Seedling.

*Seed parent.*—"Tom Brown".

*Pollen parent.*—"Over the Rainbow".

Class: Miniature.

The following observations are made of specimens grown outdoors in Dallas County, Tex., during the month of August.

1. FLOWER

Blooming habit: Continuous.

A. Bud:

(1) *Size.*—Medium.

(2) *Form.*—Ovoid, long.

(3) *Color.*—After sepals fall, orient pink, near 36B to D.

(4) *Sepals.*—Slightly longer than bud with few appendages.

2

(5) *Peduncle.*—Length — 1 to 1½ inches. Aspect — Upright. Strength — Erect. Color — Near 191A.

B. Bloom:

(1) *Size.*—Average size when fully expanded — About 1½ inches.

(2) *Borne.*—Singly and occasionally several together in sprays.

(3) *Form.*—High centered becoming flat upon opening, petals roll backward and under, outer petals reflex to points.

(4) *Petalage.*—Number of petals under normal conditions — About 40.

(5) *Color.*—After sepals fall and petals unfurl, predominant color of petal top surfaces is azalea pink 38B to 38A with darker toned 38A appearing at flower centers where petals bunch and is seen mainly when flowers open. Color is relatively constant and unfading. Outer petals display some tonal variation, primarily toward petal edges. Slight veining with deeper tones can also be seen.

C. Petals:

(1) *Texture.*—Thick.

(2) *Appearance.*—Inside satiny, outside satiny.

(3) *Form.*—Fan shaped often with rounded edges.

(4) *Arrangement.*—Imbricate.

(5) *Petaloids in center.*—Few.

(6) *Persistence.*—Drop off cleanly.

(7) *Fragrance.*—Slight.

(8) *Lasting quality.*—Very long lasting on plant (5 to 7 days) and long lasting (4 to 5 days) as cut flower.

2. REPRODUCTIVE ORGANS

A. Stamens, filaments and anthers:

(1) *Arrangement.*—Regularly arranged around styles.

(2) *Color.*—Light yellow.

B. Pollen:

*Color.*—Yellow.

C. Styles: Bunched, uneven length, reddish color.

D. Stigmas:

*Color.*—Pale yellow.

E. Hips: Globular, about ½ inch, orange red, seeds occasionally protrude.

3. PLANT

A. Form: Upright.

B. Growth: Vigorous, uniform.

*Height attained.*—About 12 to 18 inches.

C. Foliage: Compound 5 to 7 leaflets.

(1) *Size.*—Medium.

(2) *Quantity.*—Abundant.

(3) *Color.*—New foliage: Upper side — Near to 187A. Under side — Near to 187B. Old foliage: Upper side — Near 131A. Under side — Near 133B.

(4) *Shape.*—Oval, pointed.

(5) *Texture.*—Upper side is semi-glossy and under side is matte.

(6) *Edge.*—Serrate.

(7) *Serration.*—Simple.

(8) *Leaf stem.*—Color — Reddish green. Under side — Green.

(9) *Stipules.*—Medium, slightly bearded.

(10) *Resistance to disease.*—Blackspot — Good. Mildew — Good.

D. Wood:

(1) *New wood.*—Color — Near 187A. Bark — Smooth.

(2) *Old wood.*—Color — Near 133A. Bark — Smooth.

E. Thorns:

(1) *Thorns.*—Quantity (main stalk) — Ordinary. On laterals from stalk — few. Form — Ordinary. Length — Medium. Color — Reddish. Position — Regular.

(2) *Prickles.*—None.

F. Winter hardiness: Needs ordinary protection in severe climate.

I claim:

1. A new and distinct variety of rose plant of the miniature rose class, substantially as shown and described, characterized particularly by attractive azalea pink flowers with inner petals rolling downward and outer petals reflexing to star-like points and with flower color which remains substantially constant and unfading.

* * * * *